US011832923B2

(12) United States Patent
Lange et al.

(10) Patent No.: US 11,832,923 B2
(45) Date of Patent: *Dec. 5, 2023

(54) DEVICE FOR MONITORING BLOOD FLOW

(71) Applicant: IdaHealth, Inc., Lewes, DE (US)

(72) Inventors: Philippe Lange, Liège (BE); Giovanni Amoroso, Haarlem (NL); David Lawrence Camp, Jr., Kampenhout (BE); Gabriele Buttignol, Grevenmacher (LU); Gerrit de Vries, Kampenhout (BE)

(73) Assignee: IdaHealth, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 16/992,223

(22) Filed: Aug. 13, 2020

(65) Prior Publication Data
US 2020/0367763 A1 Nov. 26, 2020

Related U.S. Application Data

(63) Continuation-in-part of application No. 16/471,823, filed as application No. PCT/EP2017/079918 on Nov. 21, 2017, now Pat. No. 11,426,083.

(30) Foreign Application Priority Data

Dec. 21, 2016 (BE) .................. 2016/5953

(51) Int. Cl.
A61B 5/026 (2006.01)
A61B 5/00 (2006.01)
(52) U.S. Cl.
CPC .......... A61B 5/026 (2013.01); A61B 5/6824 (2013.01); A61B 5/6828 (2013.01);
(Continued)

(58) Field of Classification Search
CPC ..... A61B 5/0205; A61B 5/026; A61B 5/0295; A61B 5/6824; A61B 5/6828;
(Continued)

(56) References Cited

U.S. PATENT DOCUMENTS 4,258,720 A * 3/1981 Flowers ............... A61B 5/1073
600/500
4,966,155 A * 10/1990 Jackson ............... A61B 5/1135
600/484

(Continued)

FOREIGN PATENT DOCUMENTS

EP 2581037 A1 4/2013
JP H0528309 U 4/1993
(Continued)

OTHER PUBLICATIONS

Xi et al., "Ultrathin and wearable Microtubular Epidermal Sensor for Real-Time Physiological Pulse Monitoring", 2017, Advanced Materials Technologies, vol. 2, p. 1700016; consisting of 8-pages.

(Continued)

Primary Examiner — Allen Porter
Assistant Examiner — Skylar Lindsey Christianson
(74) Attorney, Agent, or Firm — Christopher & Weisberg, P.A.

(57) ABSTRACT

A medical device for measuring blood flow through a blood vessel of a mammal includes a conductive elastomer having a variable resistance. A frame is at least partially surrounding at least a portion of the conductive elastomer, the conductive elastomer is suspended within the frame. A mechanical amplification element is slidably engaged to the conductive elastomer, the mechanical amplification element being configured to slide within the frame and to contact skin of the mammal over the blood vessel when the frame is positioned over the blood vessel, the mechanical amplification element (Continued)

being configured to be displaced when the artery pulsates and changes the resistance of the elastomer.

17 Claims, 6 Drawing Sheets

(52) U.S. Cl.
CPC .......... *A61B 5/6829* (2013.01); *A61B 5/6833* (2013.01); *A61B 5/742* (2013.01); *A61B 2562/166* (2013.01)

(58) Field of Classification Search
CPC ..... A61B 5/6829; A61B 5/6833; A61B 5/742; A61B 2562/166
See application file for complete search history.

(56) References Cited

U.S. PATENT DOCUMENTS

| | | | |
|---|---|---|---|
| 9,609,921 | B1 | 4/2017 | Feinstein |
| 10,076,251 | B2 | 9/2018 | Tu et al. |
| 2008/0300503 | A1 | 12/2008 | Lee et al. |
| 2015/0186609 | A1* | 7/2015 | Utter, II ................. G16H 20/30 600/301 |
| 2017/0281082 | A1 | 10/2017 | Khine et al. |
| 2018/0092550 | A1* | 4/2018 | Sprenger ................. A61B 7/04 |
| 2018/0184923 | A1 | 7/2018 | Tal et al. |

FOREIGN PATENT DOCUMENTS

| | | |
|---|---|---|
| JP | H08154906 A | 6/1996 |
| JP | 2006270610 A | 10/2006 |
| WO | 2015172897 A1 | 11/2015 |
| WO | 2015193045 A1 | 12/2015 |
| WO | 2018114180 A1 | 6/2018 |

OTHER PUBLICATIONS

Product Data Sheet 3M, Conductive Film Products, 2004, Retrieved from the internet: URL:http://documents.staticcontrol.com/pdf/2004.pdf.

International Search Report and Written Opinion dated Dec. 9, 2020, for corresponding International Application No. PCT/US2020/046068; consisting of 16-pages.

International Search Report and Written Opinion dated Feb. 2, 2018, for corresponding International Application No. PCT/EP2017/079918; International Filing Date: Nov. 21, 2017 consisting of 10-pages.

Non-Final Office Action dated Jun. 22, 2021 for corresponding U.S. Appl. No. 16/471,823; consisting of 22-pages.

Indian Office Action dated Dec. 3, 2021, for corresponding Indian Patent Application No. 201917026291; consisting of 6-pages.

Japanese Notice of Reasons for Refusal dated Apr. 3, 2023, for corresponding Japanese Patent Application No. 2019-533447; consisting of 16-pages.

* cited by examiner

DEVICE FOR MONITORING BLOOD FLOW

CROSS-REFERENCE TO RELATED APPLICATION

This application is a continuation-in-part of U.S. application Ser. No. 16/471,823, filed Jun. 20, 2019, which claims priority to International Application No. PCT/EP2017/079918 filed on Nov. 21, 2017, titled EQUIPMENT FOR MONITORING BLOOD FLOW AND RESPIRATORY FLOW, which is related to and claims priority to Belgian Patent Application No. 2016/5953 filed on Dec. 21, 2016, the entirety of which is incorporated by reference herein.

FIELD

The present technology is generally related to devices for measuring and monitoring blood flow through a blood vessel.

BACKGROUND

Cardiac catherization is a minimally invasive procedure used to diagnose or treat cardiac conditions. For example, percutaneous coronary interventions (PCI) are used to treat blockages in the heart with, for example, balloon angioplasty, to improve blood flow. The catheter is fed through a larger artery for example, the femoral artery, and advanced toward the vascular or cardiac site of interest for treatment. Owing to the distance travelled and the risk of bleeding, physicians often use the radial artery as the access point for PCI as opposed to the femoral artery. However, as with any surgical procedure, there is risk of damage to the blood vessel such as arterial occlusion.

SUMMARY

The techniques of this disclosure generally relate to devices for measuring and monitoring blood flow through a blood vessel.

In one aspect, a medical device for measuring blood flow through a blood vessel of a mammal includes a conductive elastomer having a variable resistance. A frame is at least partially surrounding at least a portion of the conductive elastomer, the conductive elastomer is suspended within the frame. A mechanical amplification element is slidably engaged to the conductive elastomer, the mechanical amplification element being configured to slide within the frame and to contact skin of the mammal over the blood vessel when the frame is positioned over the blood vessel, the mechanical amplification element being configured to be displaced when the blood vessel pulsates and changes the resistance of the conductive elastomer.

In another aspect of this embodiment, the mechanical amplification element slides a predetermined distance within the frame.

In another aspect of this embodiment, the mechanical amplification element defines an atraumatic skin contact surface.

In another aspect of this embodiment, the mechanical amplification element defines an aperture opposite the atraumatic skin contact surface, and wherein the conductive elastomer is slidably received within the aperture.

In another aspect of this embodiment, wherein the frame is configured to flex around a portion of at least one from the group consisting of a arm and an leg of the mammal.

In another aspect of this embodiment, the mechanical amplification element is slidable within the frame from a first position in which the sensor does not measure blood flow through the blood vessel to a second position in the sensor measures blood flow through the blood vessel.

In another aspect of this embodiment, the device further includes an adhesive patch coupled to the frame and adherable to skin of the mammal.

In another aspect of this embodiment, the device further includes a controller in communication with and coupled to the sensor.

In another aspect of this embodiment, the device further includes conductive electrical pathways disposed between the patch and frame.

In another aspect of this embodiment, the mechanical amplification element includes a gripping element extending outward therefrom.

In one aspect, a medical device for measuring blood flow through a blood vessel of a mammal includes a conductive elastomer having a variable resistance. A frame substantially surrounds at least a portion of the conductive elastomer, the frame includes a first at least substantially closed loop portion adjacent a second at least substantially closed loop portion. A first mechanical amplification element is slidably coupled to the conductive elastomer and is disposed within the first at least substantially closed loop portion. A second mechanical amplification element is slidably engaged to the conductive elastomer and disposed within the second at least substantially closed loop portion. The first and second mechanical amplification element are configured to slide within their respective one of the first at least substantially closed loop portion and the second at least substantially closed loop portion and to contact skin of the mammal over the respective blood vessel when the frame is positioned over the respective blood vessel, the first and second mechanical amplification elements being to be displaced when the respective blood vessel pulsates and changes the resistance of the conductive elastomer In another aspect of this embodiment, each of the first and second mechanical amplification elements defines an atraumatic skin contact surface.

In another aspect of this embodiment, each of the first and second mechanical amplification elements defines an aperture opposite the atraumatic skin contact surface, and wherein the conductive elastomer is slidably received within the aperture.

In another aspect of this embodiment, the frame is configured to flex around a portion of at least one from the group consisting of a wrist and an ankle of the mammal.

In another aspect of this embodiment, the frame is composed of a flexible plastic.

In another aspect of this embodiment, the device further includes and adhesive patch coupled to the frame and adherable to skin of the mammal.

In another aspect of this embodiment, the device further includes a controller in communication with and coupled to the conductive elastomer.

In another aspect of this embodiment, the device further includes conductive electrical pathways disposed between the patch and frame.

In another aspect of this embodiment, wherein each of the first and second mechanical amplification elements includes a gripping element extending outward therefrom.

In one aspect, a medical device for measuring blood flow through a blood vessel of a mammal includes a conductive elastomer having a variable resistance. A frame surrounds at least a portion of the conductive elastomer, the frame includes a first at least substantially closed loop portion adjacent a second at least substantially closed loop portion. A first mechanical amplification element is slidably coupled to the conductive elastomer and disposed within the first at least substantially closed loop portion. A second mechanical amplification element is slidably coupled to the conductive elastomer and disposed within the second at least substantially closed loop portion. The first and second mechanical amplification element are configured to slide within their respective one of the first at least substantially closed loop portion and the second at least substantially closed loop portion and to contact skin of the mammal over the respective blood vessel when the frame is positioned over the respective blood vessel, the first and second mechanical amplification elements are configured to be displaced when the respective blood vessel pulsates and changes the resistance of the conductive elastomer. An adhesive patch is coupled to the frame and adherable to the skin of the mammal, the adhesive patching defines at least a substantially closed loop about the wrist of the mammal. A printed circuit board (PCB) is disposed between the patch and the frame. A controller is coupled to the sensor and the PCB and configured to be disposed on at least a portion of wrist of the mammal, the controller includes a display configured to display blood flow measurements through the blood vessel The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
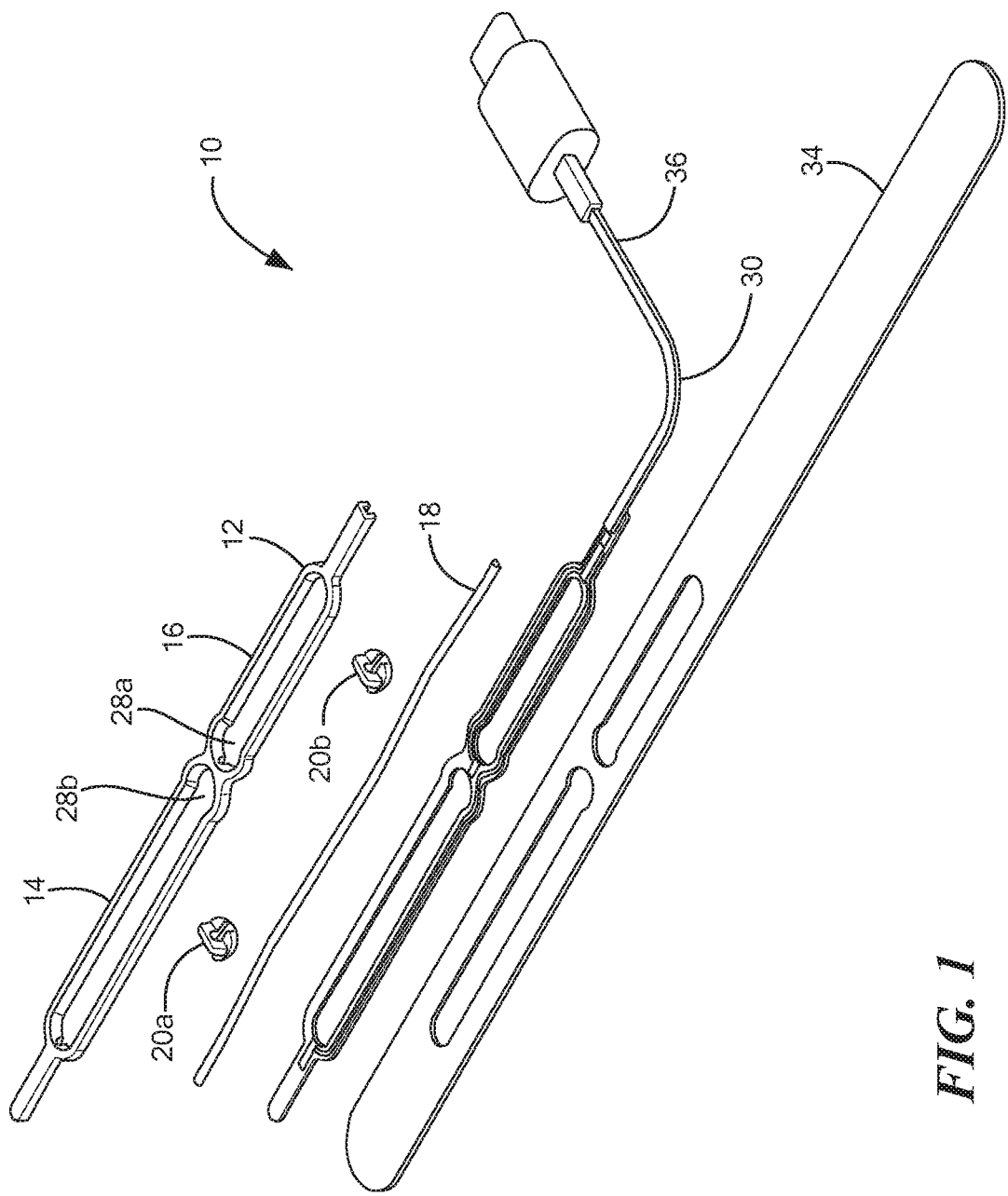
FIG. 1 is a disassembled view of a device for measuring and monitoring blood flow through a blood vessel.
Figure 2A:
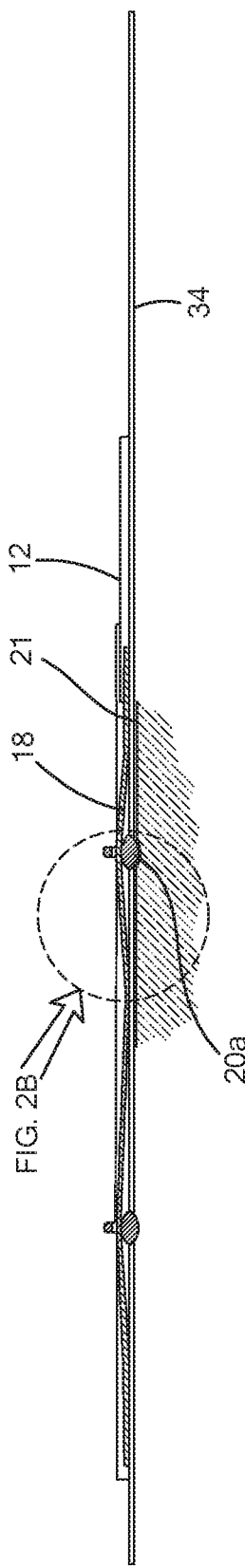
FIG. 2A is a side view of the assembled device shown in FIG. 1.
Figure 2B:
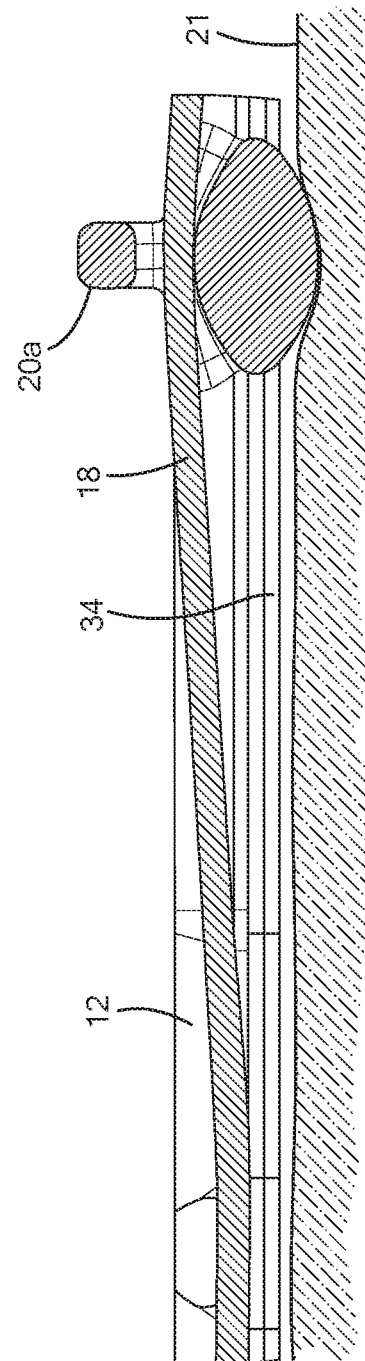
FIG. 2B is a zoomed in view of the device shown in FIG. 2A.

Referring now to the drawings in which like reference designators refer to like elements, there is shown in FIGS. 1-2A-2B an exemplary device for measuring and monitoring blood flow through a blood vessel and designated generally herein as "10." In the configuration shown in FIG. 1 the device is sized and configured to be at least partially wrapped around a mammal's wrist, for example, a human or animal. In other configurations, the device may be sized and configured to be positioned over the skin over any blood vessel, whether artery or vein within the body of the mammal. The device 10 includes a frame 12 sized and configured to contour the skin of the mammal. The frame 12 may be rigid or flexible, and in one configuration is composed of a flexible plastic. The frame 12 may define at least one substantially closed loop. For example, as shown in FIGS. 1 and 2 the frame includes a first substantially closed loop portion 14 adjacent to a second substantially closed loop portion 16. Although shown as two loops, it is contemplated that the frame 12 may include any number of loops.

Figure 7:
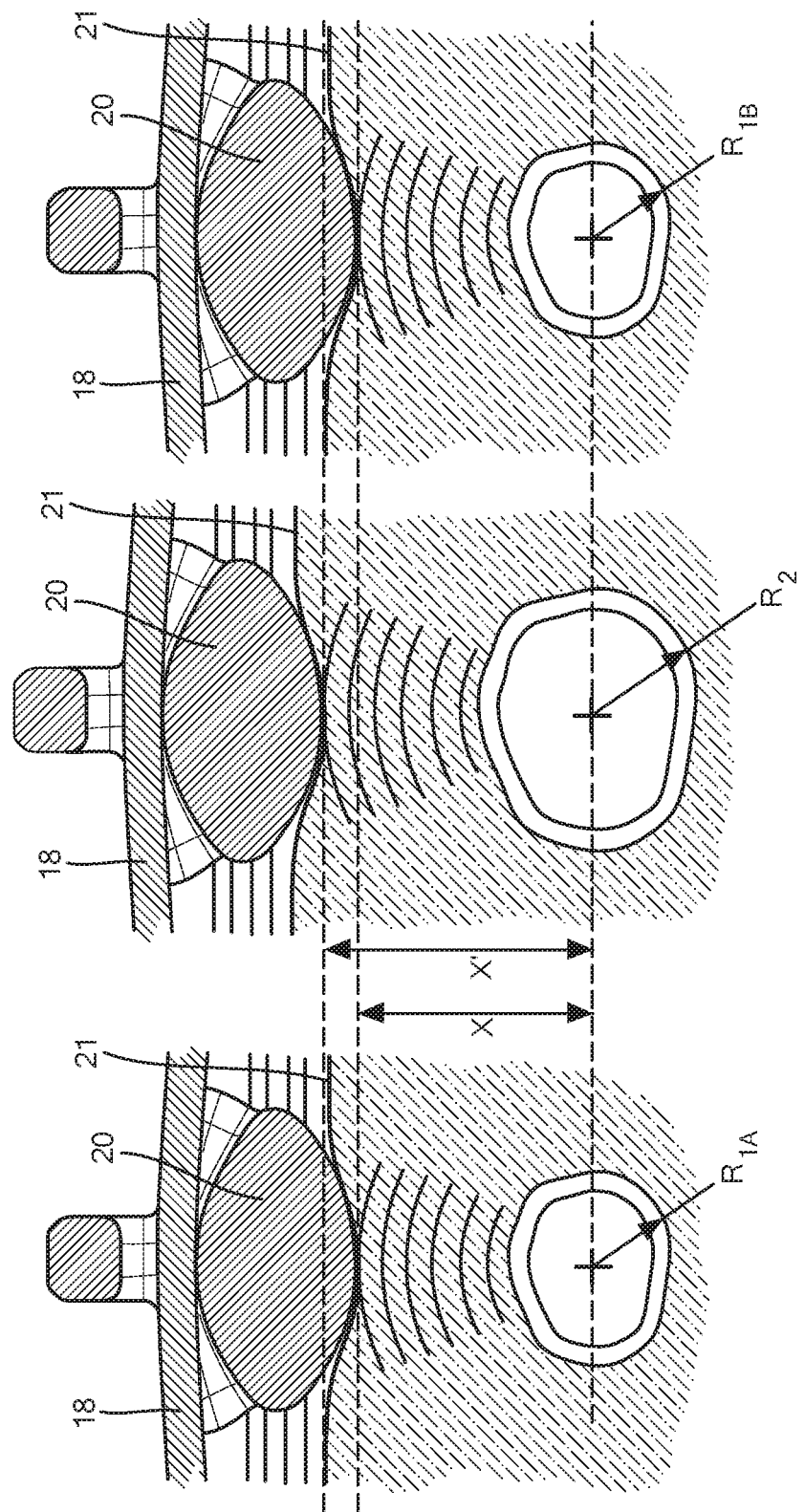
FIG. 7 is a cross-sectional view showing the mechanical amplification element shown in FIG. 3 being displaced by a pulsating blood vessel.

Extending through the frame 12 is a sensor 18 configured to measure a signal indicative of blood flow through a blood vessel. In particular, the sensor 18 is a conductive elastomer having a variable resistance. That is, the resistance of the sensor 18 changes as it is stretched, which can be measured and correlated into a flow measurement, as discussed in more detail in co-pending U.S. Patent Publication No. 2020/0093378 the entirety of which is expressly incorporated by reference herein. In the configuration shown in FIGS. 1 and 2A-2B, the sensor 18 extends through a center of the frame 12 into both the first substantially closed loop portion 14 and the second substantially closed loop portion 16. Disposed along and in communication with the sensor 18 are one or more mechanical amplification elements 20. The mechanical amplification elements 20 are configured to slide along the sensor 18 within the frame 12, and therefore a predetermined distance based on the size of the respective substantially closed loop portion 14, 16 and to contact skin of the mammal over the blood vessel when the frame 12 is positioned over the blood vessel. In particular, the mechanical amplification elements 20, which may be composed of any rigid non-conductive material, for example, plastic, wood, polymer, stone, etc., transfer vibrational energy from the pulsating blood vessel to the sensor 18. The vibrational energy stretches the sensor 18 which changes the resistance of the sensor 18 which can be measured and correlated into a measure of flow. For example, an occluded artery, whether the ulnar or radial artery, has little to no flow and thus transfer less vibrational energy to the mechanical amplification elements 20 and thus to the sensor 18. Whereas a non-occluded artery has a higher flow and pulsates, which causes the displacement of the mechanical amplification elements 20 and changes the resistance of the sensor 18 (as shown in FIG. 7). For example, as shown in FIG. 7, when the blood vessel is relaxed, the blood vessel radius "$R_{1A}$" is and the mechanical amplification element 20 is at a distance "x" between the skin surface 21 and the blood vessel. As the blood vessel pulsates with blood flow during systole, the radius of the blood vessel increases from "$R_{1A}$" to "$R_2$" and the distance between the mechanical amplification element 20 and the blood vessel increases from distance "x" to "x'," which stretches the sensor 18. As the blood vessel relaxes during diastole, the radius of the blood vessel changes from "$R_2$" to $R_{1B}$", the distance between the mechanical amplification element 20 and the blood vessel decreases from "x'" back to "x," which relaxes the sensor 18.

In an exemplary configuration, a single mechanical amplification element 20a is included in the first substantially closed loop portion 14 of frame 12 and a single mechanical amplification element 20b is included in the second substantially closed loop portion 16 of frame 12. The mechanical amplification elements 20 may be slid over the sensor 18 to a position over the blood vessel to be measured. For example, the mechanical amplification element 20a may be positioned over the radial artery and the mechanical amplification element 20b may be positioned over the ulnar artery. The spacing between mechanical amplification elements 20 may be between 5-80 mm such that the frame 12 can accommodate any size wrist or spacing between the ulnar and radial arteries. In other configurations, mechanical amplification elements 20 may be positioned over veins in the wrist of other areas of the mammalian body.

Figure 3:
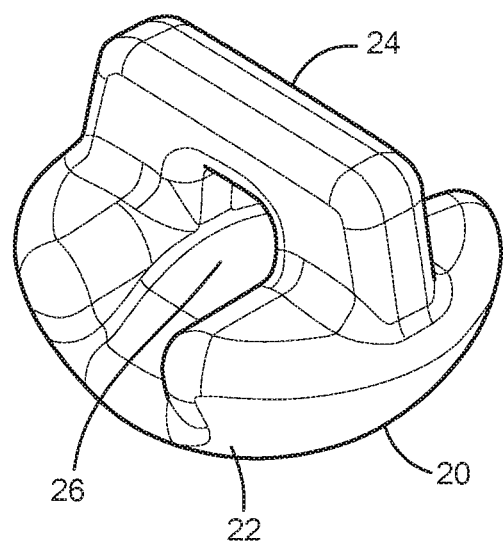
FIG. 3 is a perspective view of the mechanical amplification element show in FIG. 1.

Referring now to FIG. 3, the mechanical amplification elements 20 include an atraumatic skin contact surface 22 opposite a gripping element 24 which depends an aperture 26 therethrough. The atraumatic skin contact surface 22, which may hemispherical in shape or any atraumatic shape is configured to contact the skin over the blood vessel. In one configuration, the atraumatic skin contact surface 22 also includes a thin adhesive layer such that it sticks to the skin when positioned over the skin until moved to a different position with the gripping element 24. In an exemplary configuration, the sensor 18 is disposed within the aperture 26 such that the mechanical amplification element 20 slides along the sensor 18. Owing to the elevation of the aperture 26 at the top of the mechanical amplification element 20, the sensor 18 is pre-stretched within the mechanical amplification element 20, as shown in FIG. 2B. In some configurations, each substantially closed loop portion 14 and 16 defines an area with a wider diameter than the rest of the respective substantially closed loop portion 14 and 16. For example, the first substantially closed loop portion 14 may define a well 28a sized and configured to receive the mechanical amplification element 20a and similarly, the second substantially closed loop portion 16 may define a well 28b sized and configured to received mechanical amplification element 20b. The wells 28a and 28b are sized to allow the respective mechanical amplification elements 20 to rest within the well without placing tension on the sensor 20. In other words, the wells 28a and 28b provide a neutral position for the mechanical amplification elements 20 to rest and not measure flow before they are slid into position over the target blood vessel and measure blood flow.

Figure 4:
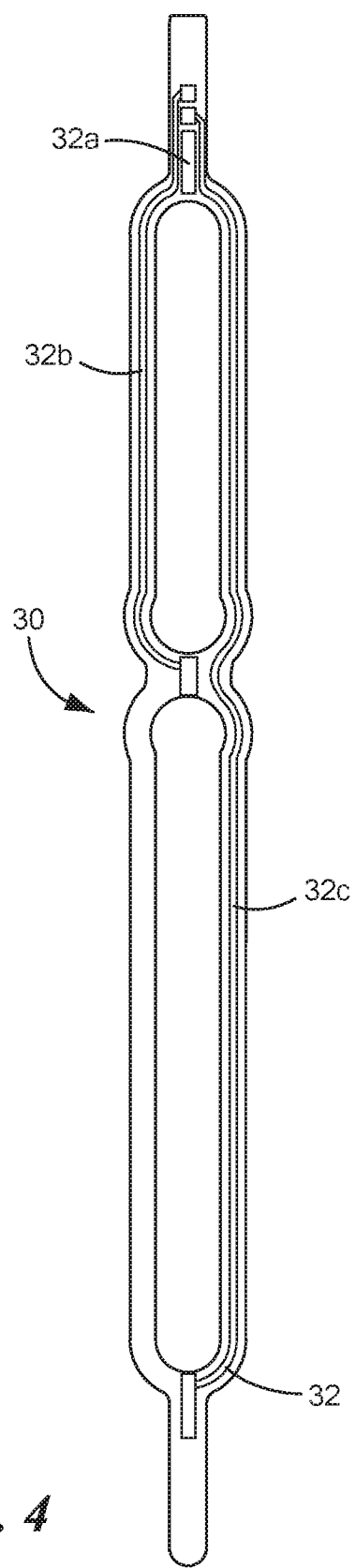
FIG. 4 is a top view of the printed circuit board shown in FIG. 1.
Figure 5:
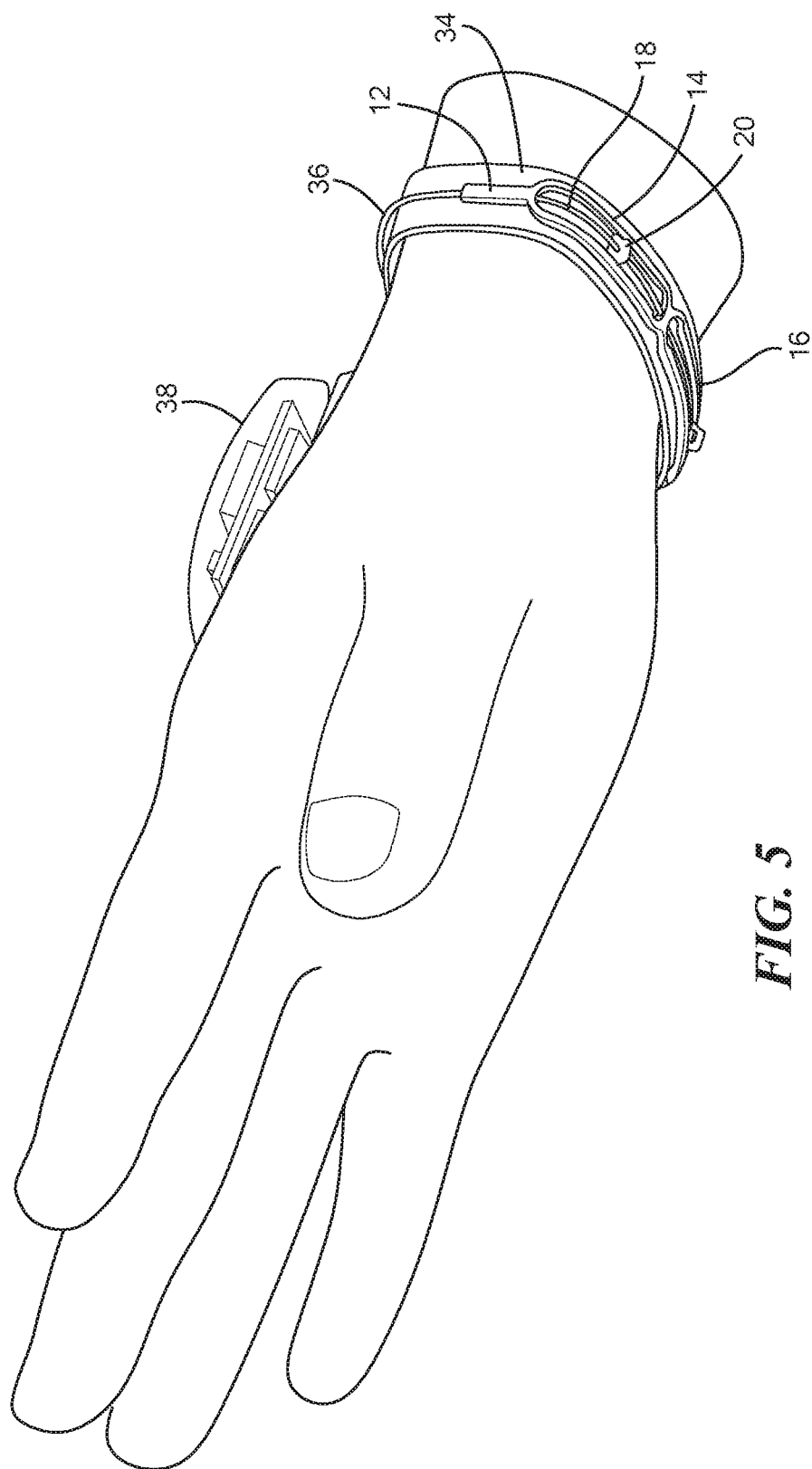
FIG. 5 is a perspective view of the assembled device shown in FIG. 1 with a controller on the surface of the wrist.
Figure 6:
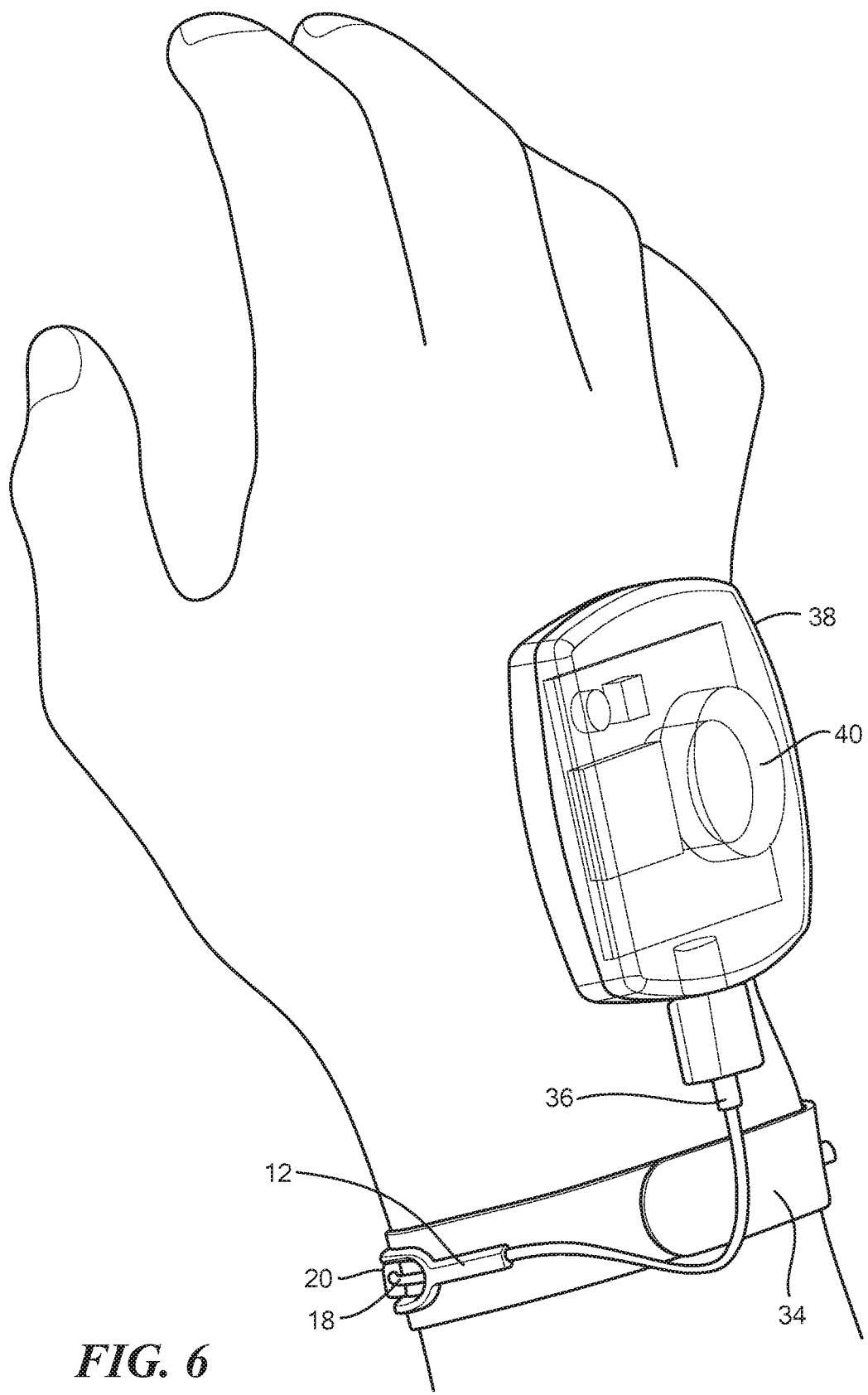
FIG. 6 is perspective view of the device shown in FIG. 5 showing the controller coupled to the sensor.

Referring back now to FIG. 1, affixed to the frame 12 is a circuit board, for example, a printed circuit board 30 (PCB) which is sized and shape commensurate with that of the frame 12. The PCB 30 may include the processing circuitry having one or more processor configured to measure and monitor a change in resistance of the sensor 18 and correlate that change in resistance to a measure of flow. In an exemplary configuration, the frame 12 is placed on top of the PCB 30 and is adhered to the PCB with glue. The PCB 30 may further include a plurality of conductors 32 (shown in FIG. 4) coupled to respective segments of the sensor 18. For example, a first of the plurality of conductors 32a may be coupled to the entirety of the sensor 18 extending through the frame 12. A second of the plurality of conductors 32b may be coupled to a portion of the sensor 18 within the first substantially closed loop portion 14 and a third of the plurality of conductors 32c may be coupled to a portion of the sensor 18 within the second substantially closed loop portion 16. In such a configuration, sensor 18 measurements can be isolated within each closed loop portion 14, 16 of the frame 12. The PCB 30 may further be adhered to an adhesive patch 34 sized and configured to be releasably adhered to skin of the mammal. In an exemplary configuration, a clinician adheres the patch 34 around the wrist of the mammal which further attaches the PCB 30 and the frame 12 around the wrist of the mammal. Further coupled to the PCB 30 is a connector 36 which extends away from the PCB 30 and is coupled to a controller 38 (shown in FIGS. 5 and 6). In an exemplary configuration, the controller 38 is sized and configured to be placed on a portion of the mammal's body, for example, on the opposite side of the wrist from the frame 12, however the controller 38 may be positioned anywhere on the device 10. The controller 38 may further include a display 40 having one or more flow indicators. In one configuration, the controller 38 may include red, yellow, and green LED indicators lights which indicate a level of flow through the measured artery. For example, an occluded radial artery may trigger a red indicator light on the controller 38. In other configurations, the controller 38 may include a display that displays the actual flow measurements and/or includes an audio alert if the blood vessel being measured is occluded. In still other configurations, the controller 38 may include a wireless transmitter (not shown) to communicate with hospital monitors, which further display flow measurements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device for measuring blood flow through a blood vessel of a mammal, comprising:
   a frame;
   a conductive elastomer having a variable resistance, the conductive elastomer being suspended within the frame;

a first rigid mechanical amplification element slidably engaged to the conductive elastomer and configured to slide in a first direction to be positioned along a length of the conductive elastomer and along a length of the frame, the first rigid mechanical amplification element being configured to slide within the frame in the first direction and to contact skin of the mammal over the blood vessel when the frame is positioned over the blood vessel, the first rigid mechanical amplification element being configured to transfer pulsations of blood in the blood vessel to the conductive elastomer in a second direction that is transverse to the first direction to cause the conductive elastomer to deform as the blood vessel pulsates; and a sensor to detect changes in the variable resistance of the conductive elastomer as the conductive elastomer deforms to generate an electrical signal indicative of the pulsation of blood in the blood vessel.

2. The device of claim 1, wherein the frame is configured to flex around a portion of at least one from the group consisting of an arm and a leg of the mammal.

3. The device of claim 1, wherein the first rigid mechanical amplification element is slidable along the frame from a first position in which the conductive elastomer is in a neutral position to a second position in the which the sensor measures blood flow through the blood vessel.

4. The device of claim 1, wherein the first rigid mechanical amplification element includes a thin adhesive layer adherable to skin of the mammal.

5. The device of claim 4, further including a controller in communication with and coupled to the conductive elastomer.

6. The device of claim 1, wherein the first rigid mechanical amplification element includes a gripping element extending outward therefrom, the gripping element configured to enable sliding of the mechanical amplification element in the first direction to a position along a length of the frame.

7. The device of claim 1, wherein the first rigid mechanical amplification element is configured to stretch the conductive elastomer during systole and to relax the conductive elastomer during diastole, the stretching and relaxing of the conductive elastomer causing a corresponding rise and fall of resistance of the conductive elastomer that is detected by the sensor.

8. The device of claim 1, wherein the first rigid mechanical amplification element includes a gripping element and an atraumatic contact surface, the gripping element configured to removably apply the atraumatic contact surface to skin over the blood vessel without wrapping the device around an appendage of a patient to which the device is applied.

9. The device of claim 1, wherein the first rigid mechanical amplification element includes an aperture, the conductive elastomer being configured to pass through the aperture and extend past each side of the aperture.

10. The device of claim 1, wherein the first rigid mechanical amplification element is configured to be positioned at a point along the frame to pre-stretch the conductive elastomer.

11. The device of claim 1, wherein the frame includes a well, the well being configured to enable the first rigid mechanical amplification to be positioned to rest within the well without placing tension on the conductive elastomer.

12. The device of claim 1, wherein the first rigid mechanical amplification element exhibits a curvature in the second direction to form an atraumatic skin contact surface to contact skin over the blood vessel.

13. The device of claim 1, further comprising a second rigid mechanical amplification element suspended within the frame and configured to slide in the first direction to be positioned along a length of the conductive elastomer and along a length of the frame relative to a position of the first rigid mechanical amplification element.

14. The device of claim 13, wherein the first rigid mechanical amplification element is configured to slide within a first closed loop of the frame and the second rigid mechanical amplification element is configured to slide within a second closed loop of the frame.

15. The device of claim 14, wherein the first closed loop and the second closed loop are positioned to enable positioning of the first rigid mechanical amplification element over the radial artery and the second rigid mechanical amplification element over the ulnar artery.

16. The device of claim 1, wherein the frame includes at least one elongated closed loop that forms an opening to receive the first rigid mechanical amplification and enable the first rigid mechanical amplification element to slide in the first direction along a length of the frame.

17. The device of claim 1, wherein the first rigid mechanical amplification element is a non-conductive material that includes at least one of rigid plastic, wood, a rigid polymer, and stone.

* * * * *